United States Patent [19]

Fleisher et al.

[11] Patent Number: 4,695,471

[45] Date of Patent: Sep. 22, 1987

[54] BREAST CYST FLUID SCREENING METHOD FOR CANCER RISK ASSESSMENT

[75] Inventors: Martin Fleisher, Glen Cove; H. Leon Bradlow, Holliswood; Morton K. Schwartz, Tarrytown, all of N.Y.

[73] Assignee: Sloan-Kettering Institute for Cancer Research, New York, N.Y.

[21] Appl. No.: 635,846

[22] Filed: Jul. 30, 1984

[51] Int. Cl.$^4$ ............................................. G01N 33/48
[52] U.S. Cl. ...................................... 436/64; 436/813
[58] Field of Search ................................. 436/64, 813

[56] References Cited

PUBLICATIONS

Leffert, Chemical Abstracts, vol. 98, 1983, No. 98:158542n.
Boynton et al., Chemical Abstracts, vol. 98, 1983, No. 98:105436y.
Davis, "Cystic Diseases of the Breast", Progress in Clinical Cancer, 3, 221–224.
Veronesi et al., Breast Cancer in Women Subsequent to Cystic Disease of the Breast, Surg., Gynecol., Obstet., 126:529–534 (1968).
Harrington, E. et al., The Association Between Gross Cysts of the Breast and Breast Cancer, Breast 7:12–17 (1981).
Bradlow, H. L., Skidmore, F. D., Schwartz et al., "Cations in Breast Cyst Fluids", in Endocrinology of Cystic Breast Disease, N.Y. (1983), p. 197.
Gairard, B. et al., "Proteins and Ionic Components in Breast Cyst Fluids" in Endocrinology of Cystic Breast Disease, N.Y. (1983), p. 191.

Primary Examiner—Barry S. Richman
Assistant Examiner—Lynn M. Kummert
Attorney, Agent, or Firm—John P. White

[57] ABSTRACT

A method for screening breast cyst fluid to identify patients having a high risk of developing breast cancer, comprising the steps of measuring the chloride ion content of breast cyst fluid aspirated from the patient; and correlating the chloride ion concentration with the risk of developing breast cancer.

2 Claims, No Drawings

BREAST CYST FLUID SCREENING METHOD FOR CANCER RISK ASSESSMENT

BACKGROUND OF THE INVENTION

The invention is concerned with a method of screening patients for increased risk of breast cancer, by measuring the chloride concentration in breast cyst fluid aspirated from cysts in the patient's breast.

Carcinoma of the breast is one of the most common malignant tumors in women. It has been reported that over 4% of all women will develop cancer of the breast during their life. At least half of these will die of the condition and/or will suffer the trauma of a mutilating operation. Cystic or fibrocystic disease is the most common benign breast lesion occurring during the middle years of life. As cancer of the breast is the most common sex-specific entity occurring in the United States, a great deal of study has been centered upon the possible relationship of cystic disease of the breast to breast cancer. Different studies have reported some correlation e.g. Davis, "Cystic Disease of the Breast: Its Relationship to Mammary Carcinoma", pages 221–224 Progress in Clinical Cancer, 3; Veronesi et al, "Breast Cancer in Women Subsequent to Cystic Disease of the Breast, *Surgery, Gynecology & Obstetrics* 529–532 (March 1968); Harington, "The Association Between Gross Cyst of the Breast and Breast Cancer, *Breast, Diseases of the Breast*", Vol. 7, No. 1, pages 13–15 (1981)). However, these articles essentially concern the correlation of the existence of breast cysts with the risk of cancer. In general, of the numerous surveys which have been made of the incidence of breast cancer in patients suffering from cystic disease, the results broadly indicate that the incidence of breast cancer is 1.7 to 5 times higher than it is in the general female population. (Veronesi et al supra at page 530).

There are several studies which are reported in the text "Endocrinology of Cystic Breast Disease" Raven Press 1983, which discuss ions in breast cyst fluid. However, none of these articles correlate the presence of ions with the possibility of gross cystic disease.

The article by Bradlow et al entitled "Cations in Breast Cyst Fluids", reports breast cyst fluid cation concentrations but does not recognize the risk potential of ion concentration. The Gairard et al article entitled "Protein and Ionic Components in Breast Cyst Fluid" correlates electrolyte composition of breast cyst fluid with other components.

SUMMARY OF THE INVENTION

The present invention provides a method for screening aspirated breast cyst fluid for chloride ion concentration. It has been found that low chloride ion concentration in breast cyst fluid can be correlated with increased risk of developing breast cancer.

More particularly, an empirical correlation between the chloride ion concentration in breast cyst fluid aspirated from patients with gross cystic disease, can be correlated with the risk of those patients for developing breast cancer. As noted above, patients suffering from cystic disease have an incidence of breast cancer 1.7 to five times higher than in the general female population. The present invention provides a screening test for identifying within the risk population, a subset population with a greater propensity for developing cancer. The screening test can be relatively simply applied at the time the breast cyst fluid is aspirated from the patient, by following a simple procedure. Thus, this screening test is expected to have widespread use in identifying patients who should be more closely monitored for occult breast disease.

DETAILED DESCRIPTION OF THE INVENTION

Samples of breast cyst fluid were obtained from patients whose subsequent medical history was documented. Each sample was tested for chloride ion concentration using an ion selective electrode and following the usual procedures for measuring chloride ions.

The data obtained from screening the breast cyst fluid samples for chloride ion concentration was reviewed and it was determined that essentially all of the samples had either "high" chloride contents of at least 65 mM/liter concentration or "low" chloride content of less than 25 mM/liter and predominantly below the sensitivity of the chloride test applied (less than 15 mM per liter). With rare exception, none of the samples fell within the 30 to 60 mM/liter chloride concentration range. An arbitrary point at 50 mM/liter was selected to divide the "high" chloride concentration samples from the "low" chloride concentration samples.

When the test results were compared against the medical histories of the patients, insofar as the medical histories were available, it was determined that, of the patients in whom breast cancer was eventually detected, over 90% had chloride concentrations in the low (below 50 mM/liter) chloride concentration range.

Based on the results of breast cyst fluid testing summarized above and initial results of further testing, the present invention provides a useful screening method which identifies patients from the high risk population of patients suffering from cystic disease, who have a still higher risk of developing breast cancer.

The present invention is accomplished by measuring chloride content of breast cyst fluid and correlating the chloride content with greater propensity of development of cancer in the patient. The dividing range between high and low risk is approximately in the 30 to 60 mM/liter range. 50 mM/liter was selected somewhat arbitrarily and, as is evident from the discussion above, this cut-off point and, in fact, the range wherein the dividing point is selected can be varied considerably without greatly affecting the screening usefulness; most of the high chloride samples were clustered above at least 65 mM/liter while most of the low test results were clustered below our detection limit of about 15 mM/liter with few ranging above 25 mM/liter.

The testing for chloride concentration can be accomplished in any usual, well-known manner. Commercial test apparatus and colorimetric chemical "kits" are readily available for chloride testing. For the tests reported herein, an ion selective electrodes was used. Known colorimetric procedures including the use of dichromate, syringaldazine, or more formal titration procedures, can also be used. The point of discrimination between high and low chloride concentration can be selected depending on the acceptable screening tolerance and the sensitivity of the chloride per se. Dilution of the sample can also be made to meet the sensitivity range of the chloride test. Samples are normally obtained when a patient seeks treatment.

If a patient has more than one cyst, each should be separately analyzed. These samples are taken from different breast cysts and may either be taken at the same time or at different times. These samples should be separately stored and separately tested. If any of the cyst fluid samples shows a low chloride content, the patient should be considered in the high risk category. There is evidence from our testing that the cyst fluid need not derive from the breast wherein the cancer has been detected, to have given a high risk screening indication.

It is contemplated that the determination of chloride ion concentration be accomplished using one of the relatively easily applied methods well known and/or commercially available. A simple test strip impregnated e.g. with a dichromate-chloride test reagent can be used. In such a case, the amount of dichromate can be adjusted to give a color change from brown to clear in the desired range defining the border between high and low chloride concentration. Such a color change would indicate high chloride ion concentration and a low risk patient. Samples can be diluted to match test sensitivities. In the case of colorimetric determinations, this has the added advantage of reducing or limiting interferring effects of the inherent breast cyst fluid.

As can be appreciated from the discussion above, the basis on which the inventive screening test was devised allows great latitude with respect to the particular designation of high and low chloride concentrations. Thus, the above is intended to be illustrative but not limiting with respect to the invention.

What is claimed is:

1. A method for screening breast cyst fluid to identify patients having a high risk of developing breast cancer, comprising the steps of measuring the chloride ion content of breast cyst fluid aspirated from the patient; and correlating the chloride ion concentration with the risk of developing breast cancer wherein said step of correlating comprises classifying a patient having breast cyst fluid with a chloride concentration above about 60 mM/liter as a low risk patient and a patient having breast cyst fluid with a chloride ion concentration of less than 30 mM/liter as a high risk patient.

2. A method for screening breast cyst fluid to identify patients having a high risk of developing breast cancer, comprising the steps of aspirating breast cyst fluid from the patient;

determining the chloride content of the aspirated breast cyst fluid; and correlating the chloride ion concentration of the breast cyst fluid with the risk of developing breast cancer wherein said step of correlating comprises classifying a patient having breast cyst fluid with a chloride concentration above about 60 mM/liter as a low risk patient and a patient having breast cyst fluid with a chloride ion concentration of less than 30 mM/liter as a high risk patient.

* * * * *

UNITED STATES PATENT AND TRADEMARK OFFICE
CERTIFICATE OF CORRECTION

PATENT NO. : 4,695,471

DATED : September 22, 1987

INVENTOR(S) : Martin Fleisher, H. Leon Bradlow, Morton K. Schwartz

It is certified that error appears in the above-identified patent and that said Letters Patent are hereby corrected as shown below:

ON THE TITLE PAGE, ITEM [73] should read
-- [73]   Assignee: change "Sloan-Kettering Institute for Cancer Research" to --Memorial Hospital for Cancer & Allied Diseases and The Rockefeller University. --.

Signed and Sealed this

Twenty-ninth Day of March, 1988

Attest:

DONALD J. QUIGG

Attesting Officer

Commissioner of Patents and Trademarks